US011823377B2

(12) United States Patent
Kawagishi

(10) Patent No.: US 11,823,377 B2
(45) Date of Patent: Nov. 21, 2023

(54) INFORMATION PROCESSING APPARATUS, INFORMATION PROCESSING METHOD, AND NON-TRANSITORY COMPUTER-READABLE STORAGE MEDIUM

(71) Applicant: CANON KABUSHIKI KAISHA, Tokyo (JP)

(72) Inventor: Masami Kawagishi, Kanagawa (JP)

(73) Assignee: Canon Kabushiki Kaisha, Tokyo (JP)

(*) Notice: Subject to any disclaimer, the term of this patent is extended or adjusted under 35 U.S.C. 154(b) by 221 days.

(21) Appl. No.: 17/069,708

(22) Filed: Oct. 13, 2020

(65) Prior Publication Data

US 2021/0027465 A1    Jan. 28, 2021

Related U.S. Application Data

(63) Continuation of application No. PCT/JP2019/015662, filed on Apr. 10, 2019.

(30) Foreign Application Priority Data

Apr. 20, 2018 (JP) .................... 2018-081763

(51) Int. Cl.
    *G06T 7/00* (2017.01)
    *G06T 7/12* (2017.01)
    (Continued)

(52) U.S. Cl.
    CPC .......... *G06T 7/0012* (2013.01); *A61B 6/5217* (2013.01); *G06T 7/12* (2017.01);
    (Continued)

(58) Field of Classification Search
    CPC ................. G06T 7/0012; G06T 7/12; G06T 2207/10081; G06T 2207/30064;
    (Continued)

(56) References Cited

U.S. PATENT DOCUMENTS

| 8,050,481 B2* | 11/2011 | Reeves ................. G06T 7/0012 |
| | | 382/128 |
| 2011/0144482 A1* | 6/2011 | Sendai ................. G06T 7/0012 |
| | | 600/425 |

(Continued)

FOREIGN PATENT DOCUMENTS

| JP | 2016214323 A | 12/2016 |
| JP | 2018061771 A | 4/2018 |

OTHER PUBLICATIONS

Chen Bin et al., "Study on Automatic Derivation of Image Findings Related to Pulmonary Nodules from Chest CT images Based on Machine Learning", Meeting Proceedings of Japanese Society of Medical Imaging Technology (CD-ROM), 35th ROMBUNNO. pp. 34, 2016.

(Continued)

*Primary Examiner* — Siamak Harandi
*Assistant Examiner* — Julius Chai
(74) *Attorney, Agent, or Firm* — Canon U.S.A., Inc. IP Division

(57) ABSTRACT

An information processing apparatus includes an image feature acquiring unit configured to acquire first image features and second image features from a medical image and a deriving unit configured to derive image findings of a plurality of items belonging to a first finding type based on the first image features and deriving image findings of a plurality of items belonging to a second finding type different from the first finding type based on the second image features that at least partly differ from the first image features.

18 Claims, 5 Drawing Sheets

(51) Int. Cl.
*G16H 50/20* (2018.01)
*G16H 30/40* (2018.01)
*A61B 6/00* (2006.01)
*G06V 10/25* (2022.01)
*G06V 10/764* (2022.01)
*G06V 10/82* (2022.01)
*A61B 3/12* (2006.01)
*A61B 5/00* (2006.01)
*A61B 5/055* (2006.01)
*A61B 6/03* (2006.01)
*A61B 8/08* (2006.01)

(52) U.S. Cl.
CPC ............ *G06V 10/25* (2022.01); *G06V 10/764* (2022.01); *G06V 10/82* (2022.01); *G16H 30/40* (2018.01); *G16H 50/20* (2018.01); *A61B 3/12* (2013.01); *A61B 5/0095* (2013.01); *A61B 5/055* (2013.01); *A61B 6/032* (2013.01); *A61B 6/037* (2013.01); *A61B 8/5223* (2013.01); *G06T 2207/10081* (2013.01); *G06T 2207/30064* (2013.01); *G06V 2201/032* (2022.01)

(58) Field of Classification Search
CPC ...... G16H 50/20; G16H 30/40; G06V 10/462; G06V 2201/032; A61B 6/5217; A61B 6/032; A61B 6/037; A61B 3/12; A61B 5/0095; A61B 5/055; A61B 8/5223
See application file for complete search history.

(56) References Cited

U.S. PATENT DOCUMENTS

2013/0051646 A1* 2/2013 Nakano .................. G16H 40/63
382/131
2016/0335764 A1* 11/2016 Kawagishi ............. G16H 70/60
2021/0319879 A1* 10/2021 Zhao ........................ G06N 3/08

OTHER PUBLICATIONS

Nakagomi K et al., "Multi-shape graph cuts with neighbor prior constraints and its application to lung segmentation from a chest CT volume", Med Image Anal., 17(1), pp. 62-77, 2013.

* cited by examiner

INFORMATION PROCESSING APPARATUS, INFORMATION PROCESSING METHOD, AND NON-TRANSITORY COMPUTER-READABLE STORAGE MEDIUM

CROSS-REFERENCE TO RELATED APPLICATIONS

This application is a Continuation of International Patent Application No. PCT/JP2019/015662, filed Apr. 10, 2019, which claims the benefit of Japanese Patent Application No. 2018-081763, filed Apr. 20, 2018, both of which are hereby incorporated by reference herein in their entirety.

BACKGROUND OF THE INVENTION

Field of the Invention

The present invention relates to the present disclosure relates to an information processing apparatus, an information processing method, and a non-transitory computer-readable storage medium.

Background Art

NPL1 describes a technique for computing features of an abnormal shadow (pulmonary nodule) in a region of interest set in a medical image (chest computed tomographic (CT) image) to derive multiple image findings related to the pulmonary nodule by using the features.

CITATION LIST

Non Patent Literature

NPL1: Chen Bin and 15 others, "Study on Automatic Derivation of Image Findings Related to Pulmonary Nodules from Chest CT images Based on Machine Learning", Meeting Proceedings of Japanese Society of Medical Imaging Technology (CD-ROM), 35th ROMBUNNO. PP-34, 2016

NPL2: Nakagomi K et al., "Multi-shape graph cuts with neighbor prior constraints and its application to lung segmentation from a chest CT volume", Med Image Anal., 17(1), pp. 62-77, 2013

However, different types of image findings are derived by uniformly using the same features, and unnecessary processing may arise depending on an image finding to be derived.

An object of the present disclosure is to improve efficiency of processing for deriving image findings.

The present disclosure is not limited to the above-described object, and another object of the present disclosure can be to achieve benefits that are derived from configurations illustrated in embodiments, which will be described later, of the invention and that are not obtained by using conventional techniques.

SUMMARY OF THE INVENTION

An information processing apparatus according to an embodiment of the present invention is characterized by including: an image feature acquiring unit configured to acquire first image features and second image features from a medical image; and a deriving unit configured to derive image findings of a plurality of items belonging to a first finding type based on the first image features and deriving image findings of a plurality of items belonging to a second finding type different from the first finding type based on the second image features that at least partly differ from the first image features.

Further features of the present invention will become apparent from the following description of exemplary embodiments with reference to the attached drawings.

DESCRIPTION OF THE EMBODIMENTS

Embodiments of the present invention will be described below with reference to the drawings.

First Embodiment

An information processing apparatus according to a first embodiment sets target regions, which are to be subjected to image analysis, for respective types of image finding (hereinafter, referred to as "finding types") in an abnormal shadow extracted from a medical image and performs image analysis of each of the regions to acquire features for the finding types. Then, the apparatus derives image findings of a plurality of items belonging to each of the finding types by using the features for the finding type. In the following description, it is assumed that a medical image is a chest X-ray CT image and image findings of a plurality of items belonging to different finding types related to an abnormal mass-like shadow (pulmonary nodule) in a lung field are acquired.

Specifically, it is assumed herein that a first finding type represents information on surroundings of the abnormal shadow (relationship with surrounding tissue), a second finding type represents the shape of the abnormal shadow, and a third finding type represents the nature of the abnormal shadow. Examples of image findings of items belonging to the first finding type include pleural retraction and arteriovenous involvement. Examples of image findings of items belonging to the second finding type include serrated edges and spiculation. Examples of image findings of items belonging to the third finding type include a calcification concentration and a cavity.

For image findings, a derived result differs in expression depending on the item. For example, the item "pleural retraction" is expressed in characters, such as "presence" or "absence", whereas the item "calcification concentration" is expressed in numerical values, such as "0%". In other words, a derived image finding may be expressed in characters or may be expressed in numerical values. Furthermore, derived results may be expressed in binary values representing, for example, "presence" and "absence", or may be expressed in multiple values representing, for example, "0 percent", "1 to 33 percent", "34 to 66 percent", "67 to 99 percent" and "100 percent".

Figure 1:
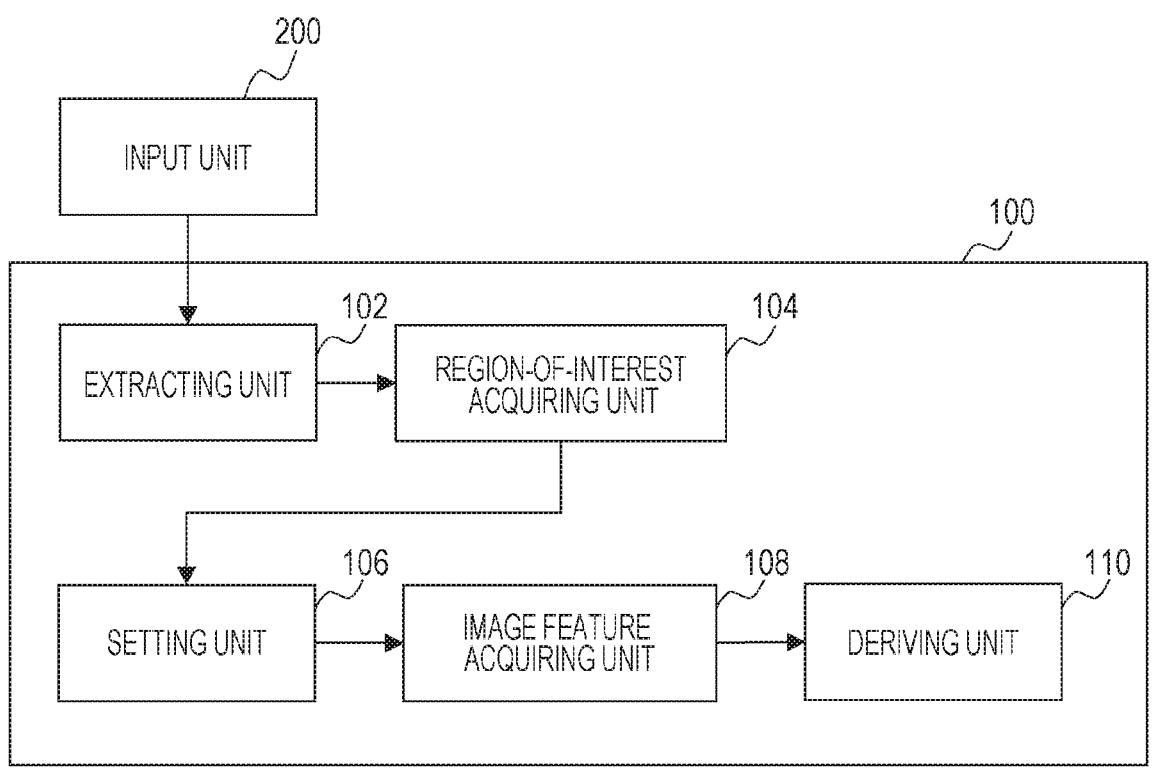
FIG. 1 is a diagram illustrating an exemplary functional configuration of an information processing apparatus.

FIG. 1 is a diagram illustrating an exemplary functional configuration of an information processing apparatus 100 according to the first embodiment. The information processing apparatus 100 corresponds to an exemplary apparatus that executes an information processing method according to this embodiment. The information processing apparatus 100 according to the embodiment is connected to an input unit 200. The input unit 200 acquires a medical image from, for example, a picture archiving and communication system (PACS) or a modality, in response to a request from the information processing apparatus 100, and inputs the acquired medical image to the information processing apparatus 100. Alternatively, the input unit 200 may be a PACS or a modality and input a necessary medical image to the information processing apparatus 100 in response to a request from the information processing apparatus 100.

The information processing apparatus 100 includes an extracting unit 102, a region-of-interest acquiring unit 104, a setting unit 106, an image feature acquiring unit 108, and a deriving unit 110. The extracting unit 102 extracts abnormal shadow candidates from the medical image inputted to the information processing apparatus 100. The region-of-interest acquiring unit 104 acquires regions of interest surrounding the respective abnormal shadow candidates. The setting unit 106 sets, based on each of the regions of interest, regions to be subjected to image analysis in the medical image. The image feature acquiring unit 108 performs image analysis of each of the regions to acquire image feature(s) of the region. The deriving unit 110 derives image findings of a plurality of items belonging to the respective finding types by using the features.

In the embodiment, the setting unit 106 sets a first region to be processed for the first finding type, a second region to be processed for the second finding type, and a third region to be processed for the third finding type. Furthermore, the image feature acquiring unit 108 performs image analysis of each of the first to third regions to acquire first image feature(s), second image feature(s), and third image feature(s). The deriving unit 110 derives image findings of a plurality of items belonging to the first finding type by using the first image features, derives image findings of a plurality of items belonging to the second finding type by using the second image features, and derives image findings of a plurality of items belonging to the third finding type by using the third image features. Although the setting unit sets the three regions in the embodiment, the number of regions to be set is not limited to this example.

Note that at least one subset of the units of the information processing apparatus 100 illustrated in FIG. 1 may be implemented as independent equipment or may be implemented as software that implements the functions. It is assumed in the embodiment that the units are implemented by software.

Figure 2:
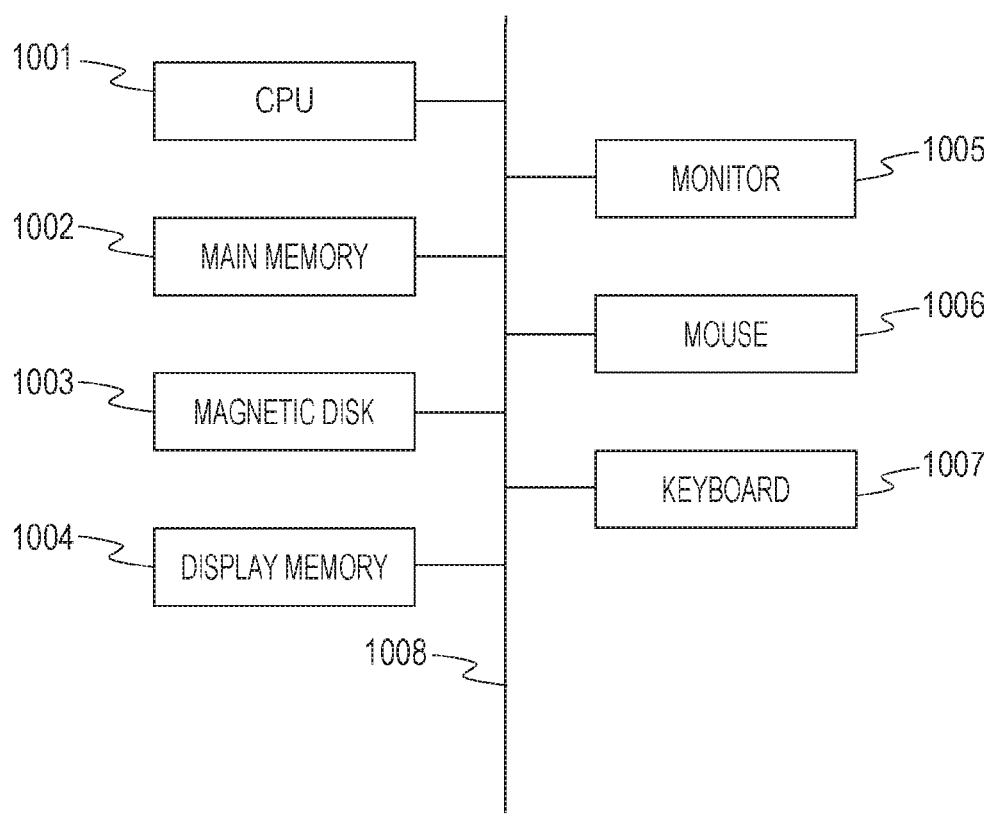
FIG. 2 is a diagram illustrating an exemplary hardware configuration of the information processing apparatus.

FIG. 2 is a diagram illustrating an exemplary hardware configuration of the information processing apparatus 100. A central processing unit (CPU) 1001 controls mainly operations of the components. A main memory 1002 stores a control program that the CPU 1001 executes and provides a work area when the CPU 1001 executes the program. A magnetic disk 1003 stores an operating system (OS), device drivers for peripheral devices, and programs for implementing a variety of application software including programs for performing processes, which will be described later. The CPU 1001 executes the programs stored in, for example, the main memory 1002 and the magnetic disk 1003, thus implementing the functions (software) of the information processing apparatus 100 in FIG. 1 and a process in a flowchart, which will be described later.

A display memory 1004 temporarily stores data to be displayed. A monitor 1005 is, for example, a cathode-ray tube (CRT) monitor or a liquid crystal display monitor, and displays, for example, an image or text based on data from the display memory 1004. A mouse 1006 and a keyboard 1007 are used to perform a pointing input and input, for example, characters, by a user. The above-described components are connected to a common bus 1008 such that the components can communicate with each other.

The CPU 1001 corresponds to an example of a processor. The information processing apparatus 100 may include at least one of a graphics processing unit (GPU) and a field-programmable gate array (FPGA) in addition to the CPU 1001. Alternatively, the information processing apparatus 100 may include at least one of the GPU and FPGA instead of the CPU 1001. The main memory 1002 and the magnetic disk 1003 correspond to examples of a memory. The information processing apparatus 100 may include, as a memory, a solid state drive (SSD).

Figure 3:
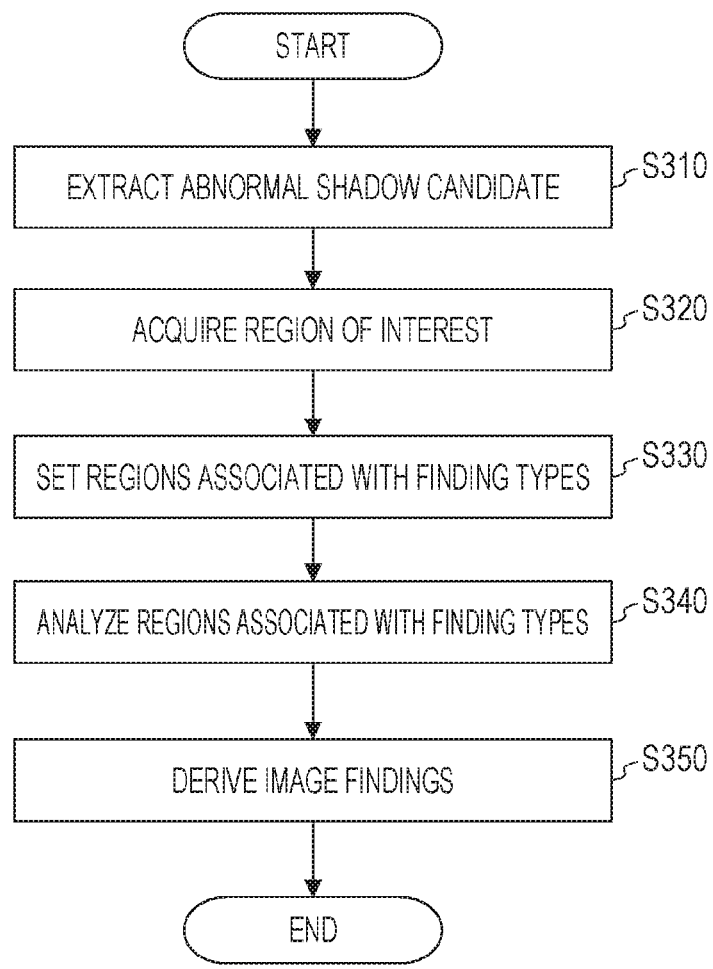
FIG. 3 is a flowchart illustrating an exemplary process of the information processing apparatus.

An overall process that the information processing apparatus 100 performs will now be described with reference to a flowchart of FIG. 3. FIG. 3 is a flowchart illustrating an exemplary process that the information processing apparatus 100 performs. In the embodiment, the CPU 1001 executes programs for implementing the functions of the units stored in the main memory 1002, thereby implementing the process of FIG. 3.

(Step S310)

In step S310, the extracting unit 102 extracts an abnormal shadow from a medical image, which is input to the information processing apparatus 100 in response to a request to the input unit 200. In the embodiment, a known computer-aided detection (CADe) technique is used to extract an abnormal shadow. For example, it is assumed herein that the abnormal shadow is a pulmonary nodule and acquired extraction results include the center position of the pulmonary nodule and a pulmonary nodule region.

(Step S320)

In step S320, the region-of-interest acquiring unit 104 acquires a region of interest in the abnormal shadow acquired by the extracting unit 102 in step S310. The region of interest may be automatically acquired by the apparatus or may be acquired in response to a region designation instruction from the user. In the embodiment, the region-of-interest acquiring unit 104 acquires, as a region of interest, a (rectangular) region circumscribing the abnormal shadow acquired in step S310. Although the rectangular region circumscribing the abnormal shadow is acquired as a region of interest in the embodiment, the region of interest may be acquired in another way. Hereinafter, the rectangular region circumscribing the abnormal shadow will be referred to as a volume of interest (VOI). For example, a rectangular region can be set in each of an axial section, a coronal section, and a sagittal section such that the region is located at the same coordinates in these sections, thereby designating a VOI. For the sake of simplicity, it is assumed in the following description that the VOI has sides having the same size, which is represented by $I_v$. This is merely an example. The width, length, and depth of the VOI may differ from each other in dimension. The shape of the VOI is not limited to a cube. The VOI may be a sphere or an ellipsoid. The region of interest does not necessarily have to circumscribe the abnormal shadow. The region of interest may be a region that surrounds the abnormal shadow and has a boundary within a predetermined distance from the edges of the abnormal shadow. Specifically, the region-of-interest acquiring unit 104 corresponds to an example of a region-of-interest acquiring unit configured to acquire, as a region of interest, a region surrounding an abnormal shadow included in a medical image.

(Step S330)

In step S330, the setting unit 106 sets the size and position of each of regions associated with the respective finding types based on the region of interest acquired by the region-of-interest acquiring unit 104 in step S320.

In the embodiment, since the first finding type represents information on surroundings of the abnormal shadow (relationship with surrounding tissue), the surroundings of the abnormal shadow may be included in a target region to be subjected to image analysis. Therefore, a cubic region that has the same center position as that of the VOI acquired by the region-of-interest acquiring unit 104 in step S320 and whose each side has a dimension of, for example, $4/3 \cdot I_V$ is set to a first region. In other words, the first region corresponds to an example of a region larger than the region circumscribing the abnormal shadow. Additionally, since $4/3 \cdot I_V$ is the product of $I_V$, which is the dimension of each side of the region of interest, multiplied by 4/3 (>1), the first region corresponds to an example of a region obtained by multiplying the region of interest by a predetermined factor greater than 1. Furthermore, since the second finding type represents the shape of the abnormal shadow, the contours of the abnormal shadow may be included in a target region to be subjected to image analysis. Therefore, the VOI, which is a cubic region circumscribing the abnormal shadow, acquired by the region-of-interest acquiring unit 104 in step S320 is set to a second region without being changed in size. In other words, the second region corresponds to an example of a region circumscribing the abnormal shadow. Furthermore, since the third finding type represents the nature of the abnormal shadow, the inside of the abnormal shadow may be set to a region to be subjected to image analysis. Therefore, a cubic region that has the same center position as that of the VOI acquired by the region-of-interest acquiring unit 104 in step S320 and whose each side has a dimension of, for example, $3/4 \cdot I_V$ is set to a third region. In other words, the third region corresponds to an example of a region smaller than the region circumscribing the abnormal shadow. Specifically, the first to third regions have a relationship such that the first region includes the second region and the second region includes the third region. The above-described sizes of the regions and the inclusion relationship between the regions are merely examples. The regions may have other sizes and another inclusion relationship. For example, the regions do not have to have a complete inclusion relationship. The regions may have a partial inclusion relationship such that one region partially (or substantially) includes another region.

Specifically, the first region may include at least part of the second region, and the second region may include at least part of the third region. Although the different three regions are set in the embodiment such that these regions have the same center, the positions of the regions may be set in another way. For example, the regions may be set such that the center position of each of the first region, the second region, and the third region is located at a distance of several voxels from the center position of the VOI acquired by the region-of-interest acquiring unit 104. Furthermore, the factors to be multiplied with the region of interest are not limited to the above-described examples.

Figure 4:
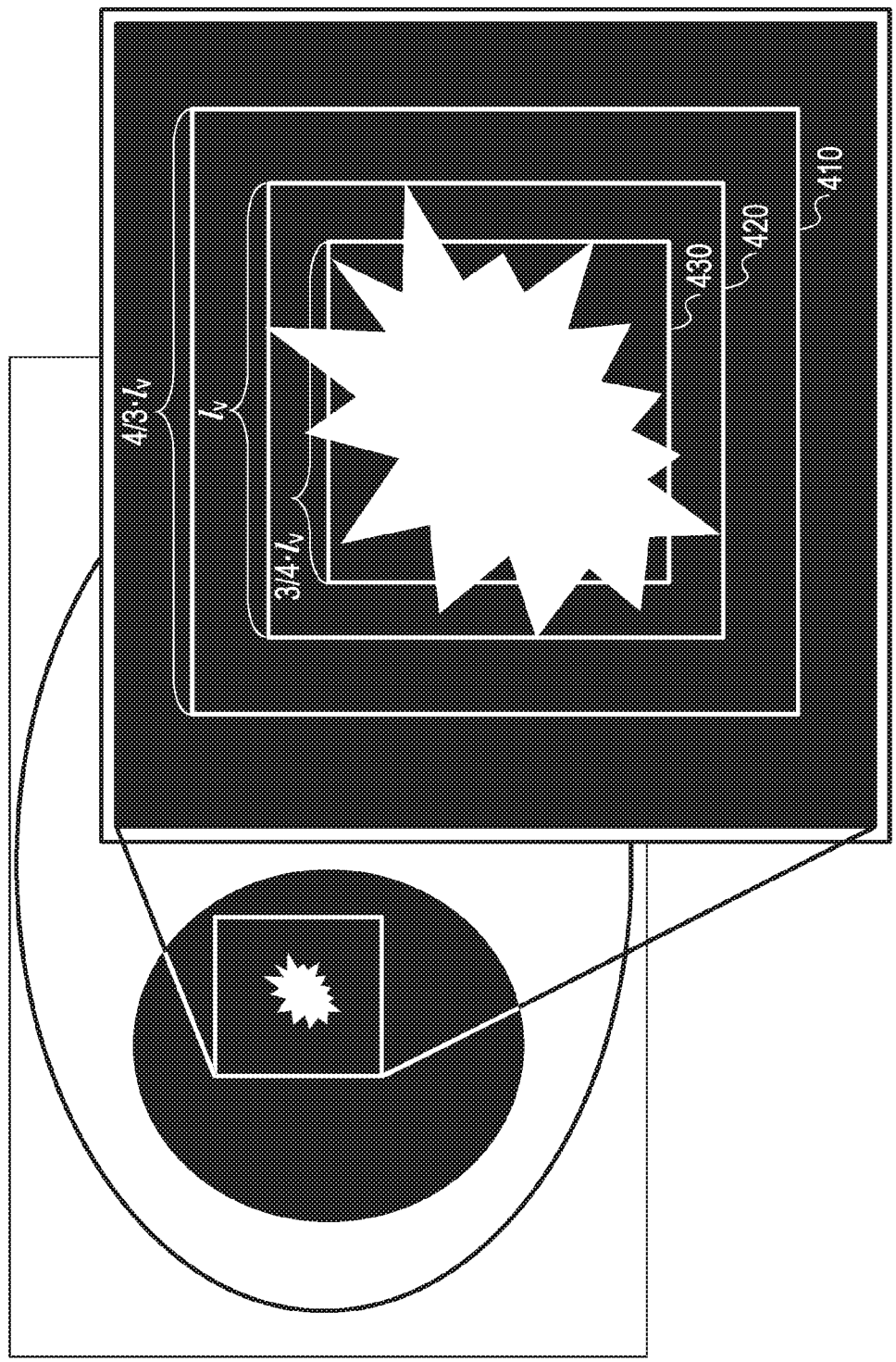
FIG. 4 is a diagram illustrating examples of target regions to be processed.

FIG. 4 is a schematic diagram illustrating a first region, a second region, and a third region. The VOI acquired by the region-of-interest acquiring unit 104 in step S320 and having respective sides of $I_V$ is a second region 420. A first region 410 is a region obtained by multiplying $I_V$, which is the dimension of each side of the VOI, by 4/3 without changing the center position. A third region 430 is a region obtained by multiplying $I_V$, which is the dimension of each side of the VOI, by 3/4 without changing the center position. Thus, the first region contains information on surroundings of the abnormal shadow (relationship with surrounding tissue) and information on the contours, which are unnecessary to obtain the nature of the abnormal shadow, is eliminated from the third region, thus achieving proper image analysis. Additionally, the elimination of unnecessary information leads to improved calculation efficiency.

(Step S340)

In step S340, the image feature acquiring unit 108 performs image analysis of each of the first to third regions set by the setting unit 106 in step S330 to acquire first to third image features associated with these regions. For example, the image feature acquiring unit 108 performs image analysis of the first region to acquire first image features, performs image analysis of the second region to acquire second image features, and performs image analysis of the third region to acquire third image features. In other words, the first image features are acquired by analyzing the first region in the medical image, and the second image features or the third image features are acquired by analyzing the second region or the third region different from the first region in the medical image. The image feature acquiring unit 108 corresponds to an example of an image feature acquiring unit configured to acquire first image features and second image features from a medical image.

The first to third regions are associated in advance with features to be computed from the respective regions. Information on association between the regions and the features to be computed is stored in, for example, the main memory 1002. The image feature acquiring unit 108 acquires features associated with the first to third regions based on the information stored in the main memory 1002.

In the embodiment, the image feature acquiring unit 108 normalizes each region to a size of, for example, 64×64×64, and analyzes the normalized region. The image size is merely an example and can be any value. Normalization is not essential processing. The image feature acquiring unit 108 masks an overlap between the first region and the second region to eliminate the overlap from a first image analysis target. Similarly, the image feature acquiring unit 108 masks an overlap between the second region and the third region to eliminate the overlap from a second image analysis target. In the embodiment, voxel values of each overlap are replaced by the same CT value (−1000 HU) as that of air so that the overlap does not have meaningful information. It is only required that the CT value used for replacement is a value reducing the influence of an overlap on image analysis. The CT value is not limited to −1000 HU and may be, for example, −999 HU. For example, if CT values ranging from −1350 HU to 150 HU are converted to pixel values of 256 gray levels ranging from 0 to 255 and the pixel values are used, voxel values of each overlap may be replaced by pixel values close to 60 because a pixel value corresponding to −1000 HU is approximately 60. Specifically, the image feature acquiring unit 108 changes the pixel values of the overlap between the first region and the second region to reduce the influence of the second region in the medical image on the first image features, and then analyzes the first region in the medical image. A region irrelevant to intended image analysis can be eliminated from an image analysis target in the above-described manner. This allows more accurate and more efficient image analysis.

Figure 5:
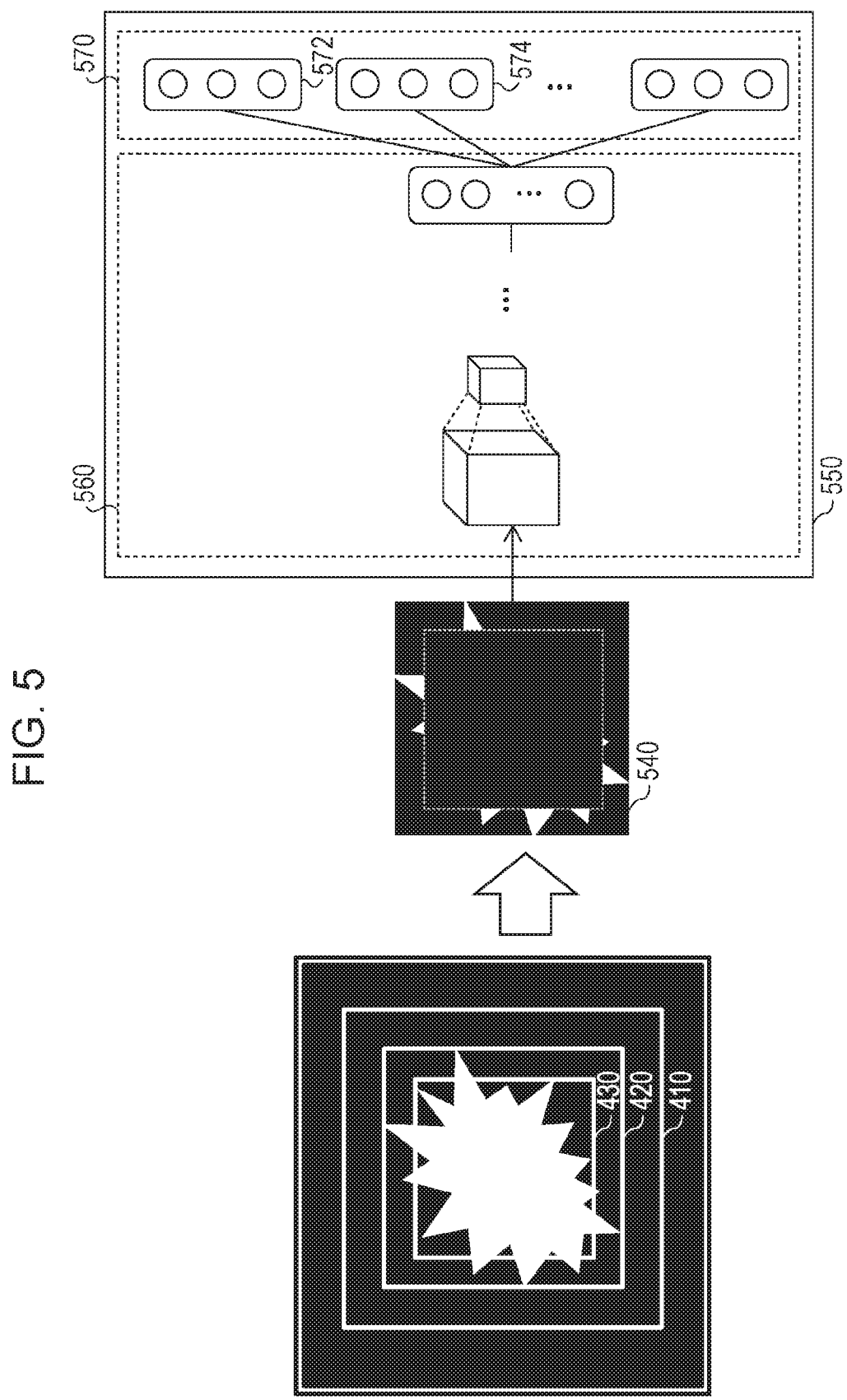
FIG. 5 is a diagram illustrating an exemplary image analysis.

FIG. 5 illustrates an example in which the second image features are acquired by image analysis in the embodiment and image findings of a plurality of items belonging to the second finding type are derived. FIG. 5 illustrates a masked image 540 obtained by masking the third region 430 inside the second region 420 with −1000 HU. Image analysis uses a deep convolutional neural network (DCNN) 550 including an image feature acquiring unit 560 to acquire second features and a second deriving unit 570 to derive a plurality of image findings belonging to the second finding type. A typical DCNN is a neural network including an input layer, multiple convolution layers, a fully connected layer, and an output layer. The DCNN 550 outputs serrated edges 572 and spiculation 574 that belong to the second finding type. As described above, a common process target region and a common image analysis technique are used for each finding type, thus enhancing the efficiency of processing.

The whole of an overlap does not have to be masked. An overlap may be partially masked so that the overlap is eliminated from an analysis target.

The above-described masking is not essential processing. For example, the image feature acquiring unit 108 may eliminate an overlap from an image analysis target by trimming without masking. Additionally, a target region to be analyzed by the image feature acquiring unit 108 may be limited to a portion of a region that does not overlap another region. For example, the image feature acquiring unit 108 may analyze only a portion of the second region that does not overlap the third region to acquire second features. Furthermore, the image feature acquiring unit 108 may analyze only a portion of the first region that does not overlap the second region to acquire first features.

(Step S350)

In step S350, the deriving unit 110 derives image findings of a plurality of items belonging to the respective finding types by using the image features acquired by the image feature acquiring unit 108 in step S340. For example, the main memory 1002 stores information in which the regions, from which the image features are extracted, in the medical image are associated with the finding types including the multiple items (image finding items). For example, the deriving unit 110 specifies, based on the information, a region in the medical image that is associated with a predetermined finding type. The deriving unit 110 acquires image features of the specified region outputted from the image feature acquiring unit 108 and derives image findings of a plurality of items belonging to the finding type.

Specifically, the deriving unit uses the first image features to derive image findings of items belonging to the first finding type, uses the second image features to derive image findings of items belonging to the second finding type, and uses the third image features to derive image findings of items belonging to the third finding type. In other words, the deriving unit corresponds to an example of deriving image findings of a plurality of items belonging to a first finding type based only on first image features acquired by analyzing a portion of a first region excluding an overlap between the first region and a second region and deriving image findings of a plurality of items belonging to a second finding type based only on second image features acquired by analyzing only the second region that is at least partly included in the first region. Furthermore, the deriving unit corresponds to an example of an acquiring unit configured to acquire a plurality of image features obtained from a medical image.

Image findings of a plurality of items belonging to each finding type may be derived based only on image features acquired by performing image analysis of an associated region or may be derived based on part of image features acquired by performing image analysis of another region in addition to the image features acquired by performing image analysis of the associated region. For example, deriving image findings of items belonging to the first finding type is not limited to deriving image findings of items belonging to the first finding type based only on the first image features obtained by image analysis of the first region, which is the associated region. Image findings of items belonging to the first finding type may be derived based on part of the second image features acquired by image analysis of the second region as well as the first image features. In other words, the deriving unit 110 corresponds to an example of a deriving unit configured to derive image findings of a plurality of items belonging to a first finding type based on first image features and image findings of a plurality of items belonging to a second finding type different from the first finding type based on second image features that at least partly differ from the first image features.

Furthermore, the deriving unit 110 may select a plurality of image features for each finding type from the first to third image features obtained by respective image analyses of the first to third regions, and derive image findings of items belonging to the finding type based on the selected image features. Additionally, the deriving unit 110 may select, based on the information indicating the association between the finding types and the image features stored in the main memory 1002, a plurality of image features for each finding type from the features obtained by image analysis of the entire image, and derive image findings of items belonging to the finding type based on the selected image features. For selection of image features, image features may be selected such that the image features partly differ between the finding types or such that the image features do not overlap each other between the finding types. In other words, the deriving unit 110 is an example of a selecting unit configured to select image features for deriving image findings of a plurality of items belonging to each of a plurality of finding types from image features such that the image features at least partly differ between the finding types, and is an example of a deriving unit configured to derive image findings of a plurality of items for each of the finding types by using the image features selected by the selecting unit. Furthermore, the deriving unit 110 corresponds to an example of a selecting unit configured to select image features such that the image features do not overlap each other between the finding types.

Furthermore, the deriving unit 110 may derive only image findings of a plurality of items belonging to either one of the first to third finding types.

In the embodiment, processing in step S340 and processing in step S350 are performed by using DCNNs. In the embodiment, a DCNN is constructed for each finding type (FIG. 5). Specifically, the DCNN 550 is constructed for the region associated with the second finding type. To analyze the region associated with the first finding type and the region associated with the third finding type to derive image findings, a DCNN (not illustrated) different from the DCNN 550 is constructed for each of these regions. Of N layers of the DCNN, (N−1) layers (560 in FIG. 5) correspond to the image feature acquiring unit 108 and the Nth layer (570 in FIG. 5) corresponds to the deriving unit 110. Although the image feature acquiring unit 108 and the deriving unit 110 are integrated with each other in this example, these units may be separate from each other. A specific example will be described later in a third modification.

In the embodiment, different image findings are derived by using image features associated with respective regions instead of uniformly using image features derived from an entire image. This leads to improved efficiency of processing for deriving image findings.

In the embodiment, a region surrounding an abnormal shadow is acquired as a region of interest, and regions associated with types of image finding (finding types) are set. Image analysis is performed for each of the regions to acquire one or more image findings included in each finding type. Since the regions are set in association with the finding types in the above-described manner, common image analysis can be performed for the same finding type. This can improve the efficiency of processing for deriving image findings. In addition, this can reduce use of features unnecessary to derive image findings, leading to improved deriving accuracy.

First Modification of First Embodiment

In the first embodiment, the region-of-interest acquiring unit 104 acquires a region of interest in step S320. However, a region of interest does not necessary have to be acquired. In this case, regions to be processed in step S330 are set without using a region of interest. For example, the pulmonary nodule region acquired by the extracting unit 102 in step S310 may be set to a second region. In addition, a region that is larger by several voxels than the boundary of a lung field including the pulmonary nodule region or the boundary of the pulmonary nodule region and that is located outside the boundary may be set to a first region. Additionally, a region that is smaller by several voxels than the boundary of the pulmonary nodule region and that is located inside the boundary may be set to a third region. The lung field can be computed by using, for example, a technique described in NPL2.

In this modification, acquisition of a region of interest is omitted, leading to shorter processing time.

Second Modification of First Embodiment

In the first embodiment, in step S340, the image feature acquiring unit 108 performs a common image analysis for each type of image finding (finding type). Different image analyses may be performed for the same finding type. For example, image analysis may be performed by using different DCNNs for each image finding without using common DCNN weights. Furthermore, a common image analysis may be performed for one finding type and different image analyses for each image finding may be performed for other finding types.

In this modification, an image analysis technique can be selected in accordance with a type of image finding (finding type) or details of an image finding, so that more appropriate image findings can be acquired.

Third Modification of First Embodiment

In the first embodiment, the image feature acquiring unit 108 and the deriving unit 110 are integrated with each other. These unit may be separate from each other. For example, the image feature acquiring unit 108 may perform image analysis of a predetermined region by using a known image processing method and the deriving unit 110 may derive image findings by using a known inference technique.

For example, for the first region, an overlap between the first region and the second region is masked, and a histogram of brightness values (CT values) in the first region is generated to obtain first features. For the second region, an overlap between the second region and the third region is filtered for edge enhancement without being masked, and the circularity or length of an edge portion is then calculated to obtain second features. In other words, the second image features correspond to an example of features acquired by applying an edge enhancement filter to a portion of the second region that does not overlap the third region and then analyzing the portion. For the third region, a Haralick features are computed and used as third features. The above-described image processing method is merely an example. Any other technique may be used.

Alternatively, an unsupervised learning technique, such as principal component analysis or self-organization map, may be used, pixel values of a region of interest may be used as inputs, and output results may be used as image features.

Image findings of the first finding type are derived by using a random forest classifier, image findings of the second finding type are derived by using a Bayesian network, and image findings of the third finding type are derived by using a support vector machine. Although the example in which image findings of the first to third finding types are derived by using different techniques has been described above, these image findings may be derived by using the same technique.

In this modification, different image processing methods or different deriving techniques can be selected for respective types of image finding (finding types). Thus, appropriate image findings can be acquired for each of the finding types.

Other Embodiments

In the above-described embodiment, the example in which the image findings related to the pulmonary nodule in the chest X-ray CT image are acquired by image analysis has been described. The present invention is not limited to this example. A target medical image may be a medical image acquired by using at least one of imaging apparatuses, such as a CT apparatus, a digital radiography apparatus, a magnetic resonance imaging (MRI) apparatus, a single photon emission CT (SPECT) apparatus, a positron emission tomography (PET) apparatus, an ultrasonic diagnostic apparatus, a fundus camera, and a photoacoustic imaging apparatus. Furthermore, a target lesion is not limited to a pulmonary nodule shadow, and may be any lesion in a subject.

The information processing apparatus according to each of the above-described embodiments may be implemented as a single apparatus or may include a plurality of apparatuses combined such that the apparatuses can communicate with each other to perform the above-described processes. Both of such configurations are included in embodiments of the present invention. The above-described processes can be executed on a shared server apparatus or servers. A plurality of apparatuses included in the information processing apparatus and an information processing system only need to be capable of communicating at a predetermined communication rate, and do not have to be located in the same facility or the same country.

According to the present disclosure, the efficiency of processing for deriving image findings can be improved.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An information processing apparatus comprising:
a memory storing a program; and
one or more processors which, by executing the program, function as:
an image feature acquiring unit configured to acquire first image features by analyzing a first region in a medical image and second image features by analyzing a second region different from the first region in the medical image, wherein the first region is a region larger than a region surrounding an abnormal shadow included in the medical image and the second region is the region surrounding the abnormal shadow; and
a deriving unit configured to derive image findings corresponding to a plurality of finding items belonging to a first finding type based on the first image features and derive image findings corresponding to a plurality of finding items belonging to a second finding type different from the first finding type based on the second image features that at least partly differ from the first image features,
wherein the first image features are commonly used for deriving the image findings belonging to the first finding type by the deriving unit and the second image features are commonly used for deriving the image findings belonging to the second finding type by the deriving unit.

2. The information processing apparatus according to claim 1, wherein the region surrounding the abnormal shadow is a region circumscribing the abnormal shadow.

3. The information processing apparatus according to claim 1, wherein the first region has a size obtained by multiplying a size of the region surrounding the abnormal shadow by a predetermined factor greater than 1 and the second region has a size equal to that of the region surrounding the abnormal shadow.

4. The information processing apparatus according to claim 1, wherein the first region is a region larger than a region circumscribing an abnormal shadow included in the medical image and the second region is the region circumscribing the abnormal shadow.

5. The information processing apparatus according to claim 1, wherein the first region includes at least part of the second region.

6. The information processing apparatus according to claim 1, wherein the first image features are acquired by analyzing a portion of the first region that does not overlap the second region.

7. The information processing apparatus according to claim 1, wherein the image feature acquiring unit acquires the first image features by changing pixel values in a portion of the first region that overlaps the second region to reduce an influence of the second region on the first image features and then analyzing the first region in the medical image.

8. The information processing apparatus according to claim 1, wherein the first image features are acquired by applying an edge enhancement filter to a portion of the first region that does not overlap the second region and then analyzing the portion.

9. The information processing apparatus according to claim 1, wherein the deriving unit derives image findings of a plurality of finding items belonging to the first finding type based only on the first image features acquired by analyzing only a portion of the first region excluding an overlap between the first region and the second region, and derives image findings of a plurality of finding items belonging to the second finding type based only on the second image features acquired by analyzing only the second region that is at least partly included in the first region.

10. The information processing apparatus according to claim 1, wherein the finding types include any of an image finding representing a relationship between an abnormal shadow and surrounding tissue, an image finding representing a shape of the abnormal shadow, and an image finding representing a nature of the abnormal shadow.

11. The information processing apparatus according to claim 1, wherein the image features acquiring unit acquires the image features by using neural networks.

12. The information processing apparatus according to claim 1, wherein the first region includes a region different from the second region in at least a part of the first region.

13. The information processing apparatus according to claim 1, wherein the first region is a region larger than the second region.

14. The information processing apparatus according to claim 1, wherein the first region and the second region are regions, each of which includes an abnormal shadow region therein.

15. The information processing apparatus according to claim 1, wherein the deriving unit derives two or more derive image findings that belong to the first finding type using the first image features and derives two or more derive image findings that belong to the second finding type using the second image features.

16. An information processing apparatus comprising:
a memory storing a program; and
one or more processors which, by executing the program, function as:
a region acquiring unit configured to acquire a first region surrounding an abnormal shadow and a second region included in the first region from a medical image;
an image feature acquiring unit configured to acquire first image features by analyzing a portion of the first region that does not overlap the second region and acquiring second image features by analyzing the second region; and a deriving unit configured to derive an image finding of an item belonging to a first finding type based on the first image features and deriving an image finding of an item belonging to a second finding type different from the first finding type based on the second image features.

17. An information processing method comprising:

acquiring first image features by analyzing a first region in a medical image and second image features by analyzing a second region different from the first region in the medical image, wherein the first region is a region larger than a region surrounding an abnormal shadow included in the medical image and the second region is the region surrounding the abnormal shadow; and deriving image findings corresponding to a plurality of finding items belonging to a first finding type based on the first image features and deriving image findings corresponding to a plurality of finding items belonging to a second finding type different from the first finding type based on the second image features that at least partly differ from the first image features, wherein the first image features are commonly used for deriving the image findings belonging to the first finding type and the second image features are commonly used for deriving the image findings belonging to the second finding type.

18. A non-transitory computer-readable storage medium storing a computer program for causing a computer to execute an information processing method comprising:

acquiring first image features by analyzing a first region in a medical image and second image features by analyzing a second region different from the first region in the medical image, wherein the first region is a region larger than a region surrounding an abnormal shadow included in the medical image and the second region is the region surrounding the abnormal shadow; and deriving image findings corresponding to a plurality of finding items belonging to a first finding type based on the first image features and deriving image findings corresponding to a plurality of finding items belonging to a second finding type different from the first finding type based on the second image features that at least partly differ from the first image features, wherein the first image features are commonly used for deriving the image findings belonging to the first finding type and the second image features are commonly used for deriving the image findings belonging to the second finding type.

* * * * *